(12) United States Patent
Rappaport et al.

(10) Patent No.: US 7,689,438 B1
(45) Date of Patent: Mar. 30, 2010

(54) METHOD, APPARATUS AND SYSTEM FOR COMMUNICATING HEALTHCARE INFORMATION TO AND FROM A PORTABLE, HAND-HELD DEVICE

(75) Inventors: Alain T. Rappaport, San Mateo, CA (US); Eliot Weitz, San Francisco, CA (US)

(73) Assignee: Microsoft Corporation, Redmond, WA (US)

( * ) Notice: Subject to any disclaimer, the term of this patent is extended or adjusted under 35 U.S.C. 154(b) by 1587 days.

(21) Appl. No.: 09/713,962

(22) Filed: Nov. 15, 2000

Related U.S. Application Data

(60) Provisional application No. 60/166,643, filed on Nov. 19, 1999.

(51) Int. Cl.
*G06Q 10/00* (2006.01)

(52) U.S. Cl. .............................. 705/2; 705/3; 600/300; 709/203

(58) Field of Classification Search ................. 705/2–3; 600/300; 709/203
See application file for complete search history.

(56) References Cited

U.S. PATENT DOCUMENTS

| | | | | |
|---|---|---|---|---|
| 5,561,446 A * | 10/1996 | Montlick | .................... | 345/173 |
| 5,687,717 A | 11/1997 | Halpern et al. | ............... | 600/300 |
| 5,732,074 A | 3/1998 | Spaur et al. | .................. | 370/313 |
| 5,772,585 A * | 6/1998 | Lavin et al. | .................. | 600/300 |
| 5,794,208 A | 8/1998 | Goltra | ........................... | 705/3 |
| 5,812,984 A | 9/1998 | Goltra | ........................... | 705/3 |
| 5,845,255 A * | 12/1998 | Mayaud | ......................... | 705/3 |
| 5,903,889 A | 5/1999 | de la Huerga et al. | ........... | 707/3 |
| 5,924,074 A * | 7/1999 | Evans | ............................. | 705/3 |
| 5,991,730 A | 11/1999 | Lubin et al. | .................... | 705/3 |
| 6,000,000 A * | 12/1999 | Hawkins et al. | ............. | 707/201 |
| 6,117,073 A * | 9/2000 | Jones et al. | ................. | 600/300 |
| 6,186,145 B1 * | 2/2001 | Brown | ......................... | 128/897 |
| 6,199,099 B1 * | 3/2001 | Gershman et al. | ........... | 709/203 |
| 6,283,761 B1 * | 9/2001 | Joao | ........................... | 434/236 |
| 6,364,834 B1 * | 4/2002 | Reuss et al. | ................. | 600/300 |
| 6,485,415 B1 * | 11/2002 | Uchiyama et al. | ........... | 600/300 |
| 2004/0049355 A1 * | 3/2004 | Maus et al. | .................... | 702/19 |

* cited by examiner

*Primary Examiner*—Vanel Frenel
(74) *Attorney, Agent, or Firm*—Turocy & Watson, LLP

(57) ABSTRACT

A method and an apparatus for communicating healthcare information utilize a set of codes to communicate healthcare data in a convenient manner. A set of codes each corresponding to respective healthcare data is generated. The set of codes is stored in a memory associated with a portable terminal. Selection of at least one code corresponding to healthcare data relevant to a patient is detected, where after the selected at least one code is wirelessly transmitted to a recipient.

9 Claims, 7 Drawing Sheets

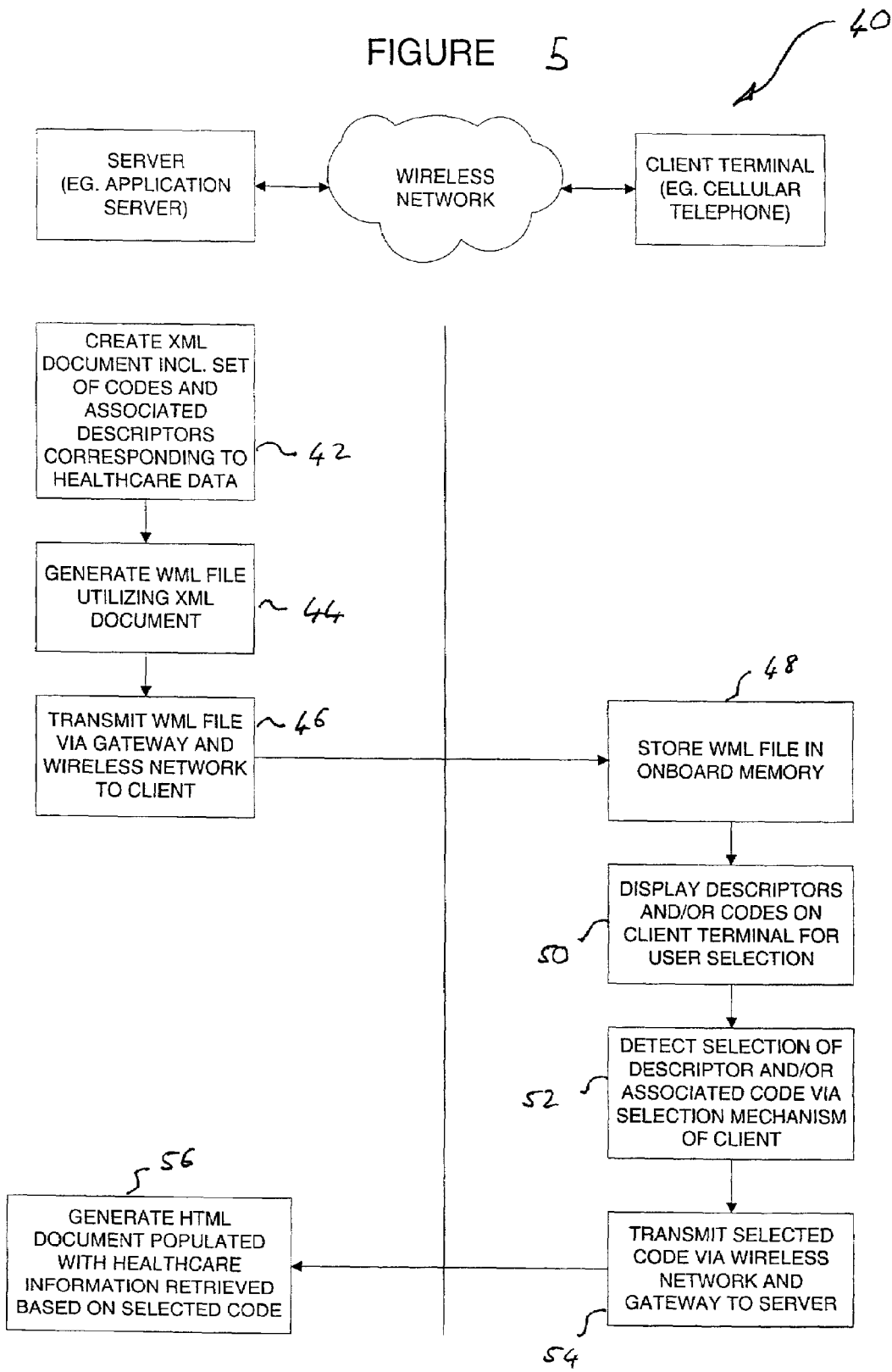

METHOD, APPARATUS AND SYSTEM FOR COMMUNICATING HEALTHCARE INFORMATION TO AND FROM A PORTABLE, HAND-HELD DEVICE

RELATED APPLICATION

This application claims the benefit of U.S. provisional application No. 60/166,643, filed Nov. 19, 1999.

FIELD OF THE INVENTION

The present invention relates to the selection and transmission of healthcare information relating to a patient.

BACKGROUND

Medical practitioners and other healthcare professionals are required frequently to record details of patients whom they are treating, in particular details of any diagnosis which may be made of a patient's condition following a consultation. However, due to the pressure under which medical practitioners operate, it may be difficult for them to find the time to enter the necessary information. It is desirable that the means available to medical practitioners for recording the relevant healthcare information should be as effortless and as seamless as possible.

SUMMARY OF THE INVENTION

According to the present invention, there is provided a method of communicating healthcare information. A set of codes each corresponding to respective healthcare data is generated. The set of codes is stored in a memory associated with a portable terminal. Selection of at least one code corresponding to healthcare data relevant to a patient is detected, where after the selected at least one code is wirelessly transmitted to a recipient.

BRIEF DESCRIPTION OF THE DRAWINGS

The features and advantages of the present invention will be more fully understood by reference to the accompanying drawings, in which:

FIG. 5 shows a simplified flow chart of basic steps in the method of the present invention.

DETAILED DESCRIPTION

Figure 1:
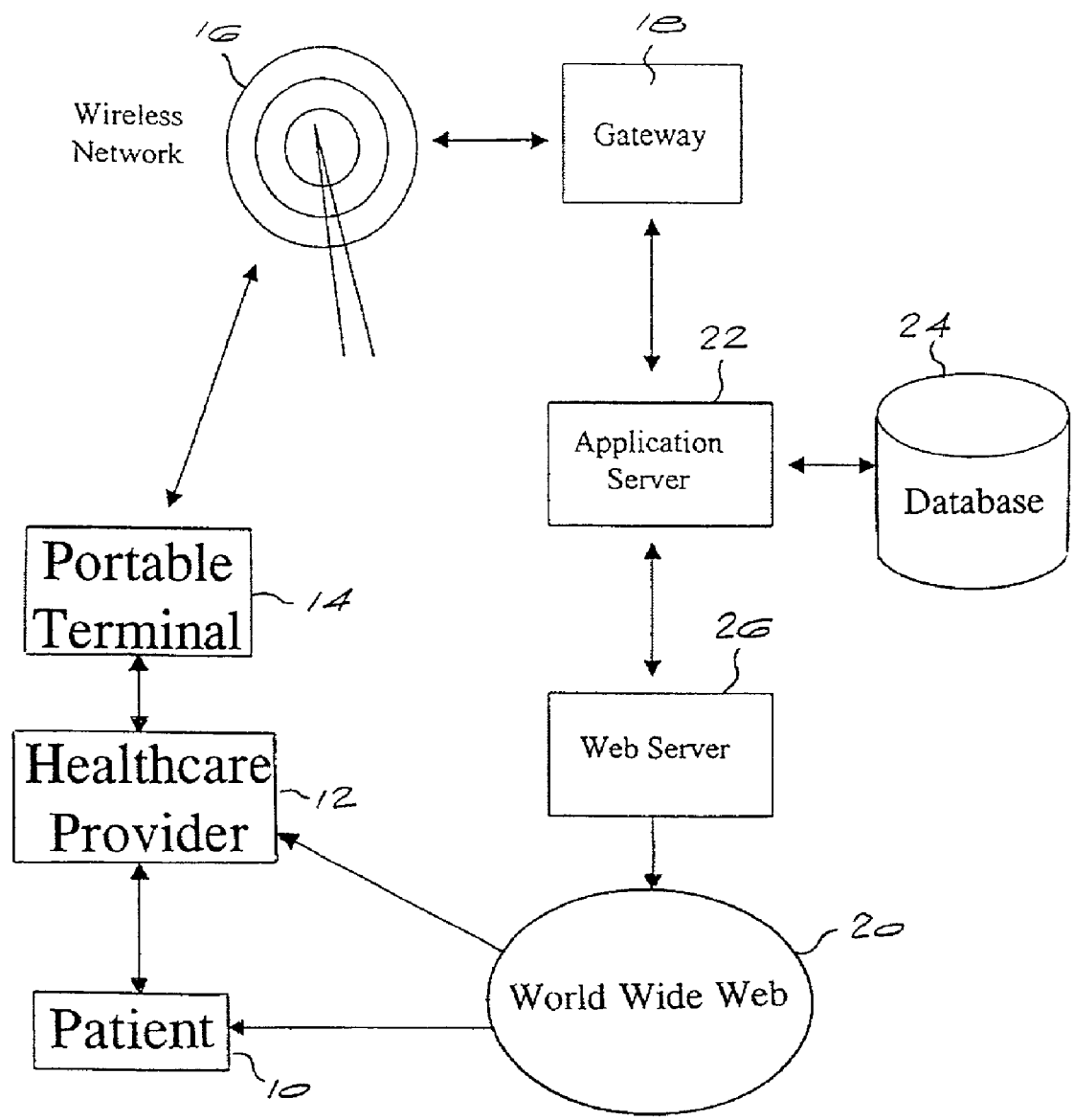
FIG. 1 shows a simplified block diagram of a system for communicating healthcare information according to the present invention.

In the following description, for the purposes of explanation and illustration, numerous specific details are set forth in order to provide a thorough understanding of the present invention. However, it will be obvious to one skilled in the art that the present invention may be practiced without the specific details. Further, the provided details provide only exemplary embodiments of the present invention.

The method and system of the present invention were designed to complement the invention described in U.S. patent application Ser. No. 09/591,769, filed Jun. 12, 2000, the contents of which are incorporated herein by reference. In essence, the present invention provides a method and system (also referred to as WirelessMed herein) for communicating healthcare information to the system described in the above-mentioned US patent application, which is particularly efficient and convenient. U.S. patent application Ser. No. 09/591,769, filed Jun. 12, 2000, describes a method and system in which information about a patient is received by the system. Typically, the information includes data identifying the patient, and diagnosis information that is based upon a diagnosis of the patient performed by a healthcare provider. When the information is received, a query function is performed which retrieves from a database a list of data sources that correspond to the information received. One or more documents are generated that contain a list of data sources retrieved from the database, and which contain information relevant to the diagnosis. These documents are then made accessible to the patient, for example, via the Internet/World Wide Web.

The method and system thus provide information to patients or healthcare consumers by providing them with relevant and personalized health related information that is tailored to their needs following their interaction with a healthcare provider. In a preferred version of the method and system, a Web document referred to as MyMedstory™ is created which is accessible by a patient via the Internet and which enables the patient to obtain further information about his or her medical condition, diagnosis and treatment, for example, following on a visit to the healthcare provider.

In the above-described patent application, a method is described by means of which healthcare providers can use a browser client program to provide information about their patients to the system. This method typically entails the use of an Internet browser and a computer terminal to access the system and communicate the relevant data. It will be appreciated that it is important to communicate the relevant data to the system as soon as possible in order for the highest possible efficiency levels to be achieved. Until the data has been so communicated, the corresponding information cannot be retrieved from the database and made available to the patient or other interested party.

The present invention addresses this need for rapid and convenient transmission of information by providing a hand-held portable terminal that can be used for selection and transmission of relevant healthcare data in the method and system described above.

Referring now to FIG. 1, a patient 10 consults a healthcare provider 12, for example, to be diagnosed in respect of an ailment or illness. On diagnosing and treating the patient, the healthcare provider selects one or more of a number of possible codes from a list of healthcare data codes stored on a portable terminal 14 and transmits the selected code or codes via a first, wireless network 16 to a gateway 18. The portable terminal 14 may be aWAP-enabled telephone, or another portable device with wireless data connectivity such as a Palm, Handspring, or Blackberry PDA device. The portable terminal 14 may also be a laptop or portable computer to a wireless data network. The wireless network 16 can be, for example, a CDMA network, a GSM network, a TDMA network, a GPRS network, a UTMS network, a proprietary wireless data network such as Mobitex, Motient, Metricom aCDPD network, a bluetooth-based network, or another wireless network with suitable capabilities. The gateway 18 serves as an interface between the wireless network 16 and a second network 20, which is typically the Internet/World Wide Web.

In the system shown in FIG. 1, the gateway 18 connects the wireless network 16 to the second network 20 via an application server 22 with an associated database 24, and a Web server 26. The use of the application server 22 and its associated database 24 makes it possible to retrieve further information which is made available to the patient, according to the invention described in U.S. patent application Ser. No. 09/591,769, filed Jun. 12, 2000. Of course, it is also possible to connect the network 16 to the network 20 directly the via the Web server 26 in a more streamlined or simplified arrangement. In this latter case, the information made available via the network 20 would correspond exactly to the healthcare data comprised by the selected code or codes.

In the illustrated example, the codes transmitted by the healthcare provider (e.g., physician) are appropriate medical codes (including but not limited to ICD-9-CM or ICD-10-CM diagnosis codes, HCPCS/CPT codes, SNOMED codes or other codifications). Each code corresponds to a respective diagnosis or other healthcare or biomedical data. The received codes may be used for a wide variety of applications, from financial and medical or clinical functions to patient information systems. The information retrieved from the database 24 by the application server or 22 is then made available to the patient or other end users in a variety of forms and via a variety of means, including but not limited to: World Wide Web pages or documents, television or web television, cellular telephones, web-enabled cellular telephones, internet appliances, game stations or other platforms.

Figure 2:
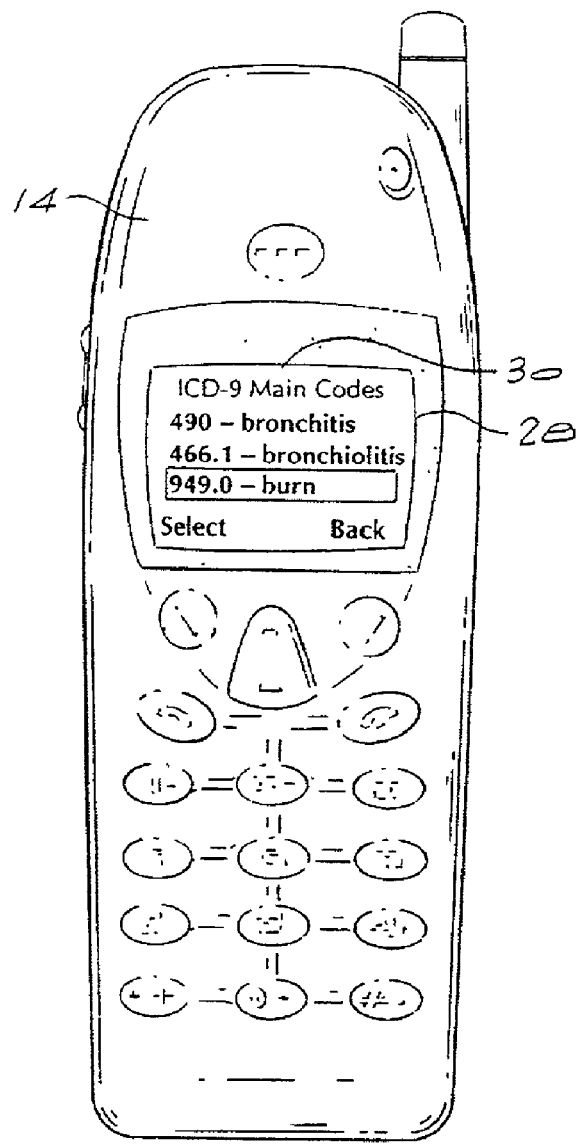
FIG. 2 shows a representation of a cellular telephone used in the system and method of the present invention, with healthcare data codes according to the present invention displayed thereon.

FIG. 2 shows an exemplary portable terminal 14 in the form of a generally conventional Web-enabled cellular telephone which has been adapted by storing a list or set of codes in the telephone memory, each code corresponding to health care data codes such as those determined by the existing ICD-9 or future ICD-10 protocols. The portable terminal 14 may execute any one of a number of known operating systems, such those developed by Nokia, Palm Computing (the Palm operating system), Psion, Symbian, Microsoft (e.g., the Pocket Windows operating system).

Figure 3:
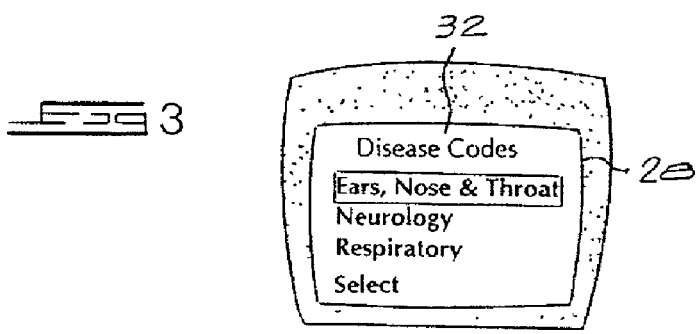
FIG. 3 shows the display of the cellular telephone of FIG. 2, indicating an alternative display scheme for lists of healthcare data codes according to the present invention.

As shown in FIG. 2, the telephone screen 28 displays a list of codes 30 which are organized alphabetically by diagnosis. Using the scrolling keys of the telephone, the desired diagnostic code can be selected and entered for transmission. FIG. 3 shows an alternative display wherein the screen 28 shows a list 32 in which the codes are organized according to medical categories or subfields, as illustrated. In this case, on selecting a category, the user is presented with further sub categories or appropriate codes in the selected category. The appropriate code or codes then selected as described above. This interface can also be used for rapid access to more detailed codes relating to the same condition. For example, bronchiolitis is coded as 466.1, but the more precise description "bronchiolitis, chronic" is coded as 506.4. Thus, the system can be used to rapidly navigate the coding classification. By way of a further example, the codes could be classified by code order, rather than alphabetical order.

By selecting the appropriate code from the displayed list, the healthcare provider can enter any common condition, procedure or other medical event or information code relevant to the patient, and communicate it to the application server 22 via the wireless cellular network 16 and the gateway 18.

There will likely be several standards for communicating information over Internet enabled telephones or other mobile devices. The following example is a "WAP" example (Wireless Application Protocol) using the "WML" language (Wireless Markup Language) derived from XML. The example code describes an instance of the WML interface for rapid, mobile, ubiquitous, easy-to-use and reliable presentation of healthcare codes. The underlying programming language to manage the communication can be WMLScript. An interpreter for WMLScript is to be included in the majority of upcoming cellular phones and will be included as well in other appliances.

In the present example, transmission of data is done via the WAP Protocol. Other existing protocols may be used. For example, the Palm VII wireless PDA or a similar wireless-capable PDS device may be used to capture the same information healthcare event information. The Palm VII has a larger screen than most cellular phones and supports a version of HTML called cHTML or "clipped HTML." Clipped HTML supports almost all of the interface elements of standard HTML including buttons, drop-down menus, check-boxes, radio buttons, etc. cHTML-based displays can be built that allow the user to easily enter the age, sex, codes, and any other healthcare event information using interface controls identical to those that would be used for data entry on a standard browser web page. Typically these devices have touch-sensitive screens that accept the input of a special stylus, sharp object, or even the tip of a finger. The user of these devices may also use one or more buttons located on the device to enter and select information presented on the device. Some popular PDAs such as the Blackberry do not have touch sensitive screen but rather a small keyboard that is used to enter and select information on the device display. FIG. 4 shows a working example of a healthcare event capture screen for a Palm VII device. The user can select the type of event from a drop-down box, enter the age and sex, select the diagnostic code, select the lab request or procedure code, and select the information target using the stylus. When the information entered on the screen by the user is complete, the user presses on a "zerosearch" button and the information is sent via the wireless data network to an Internet connected server that can process the request. An acknowledgement that the information has been received and validated is then sent back from the Internet connected server via the wireless data network to the Palm VII device.

It will be appreciated by those skilled in the art that the method and system of the present invention are independent of the specific protocol or wireless network technology employed.

Example Using WML Protocol

<?xml version="1.0"?>

<!DOCTYPE wml PUBLIC "-//WAPFORUM//DTD WML 1.1//EN"

"http://www.wapforum.org/DTD/wml_1.1.xml">

<wml>

<!—Copyright by Medstory.Com

All rights reserved. Confidential Medstory.Com

-->

<!--List of selected ICD-9-CM codes for a pediatrics practice to be selected by user and transmitted via cellular network with gateway into Internet

-->

<card id="ICD-9-CM" title="ICD-9-CM Main Codes">

<p>

<select name="code" tabindex="2">

```
<option value="789.0">789.0-abdominal pain</option>
<option value="706.1">706.1-acne</option>
<option value="349.9">349.9-attention deficit disorder</option>
<option value="309">309-adjustment reaction non-specific</option>
<option value="285.9">285.9-anemia</option>
<option value="493">493-asthma</option>
<option value="919.4">919.4-bite insect</option>
<option value="490">490-bronchitis</option>
<option value="466.1">466.1-bronchiolitis</option>
<option value="949.0">949.0-burn</option>
<option value="682.9">682.9-cellulitis dacryocystitis</option>
<option value="789.0">789.0-colic</option>
<option value="372.3">372.3-conjunctivitis</option>
<option value="850">850-concussion</option>
<option value="554.0">554.0-constipation</option>
<option value="298.9">298.9-confusion</option>
<option value="691.8">691.8-cradle cap</option>
<option value="464.4">464.4-croup</option>
<option value="375.30">375.30-dacryocystitis</option>
<option value="375.56">375.56-dacryostenosis</option>
<option value="276.5">276.5-dehydration</option>
<option value="37691.8">691.8-dermatitis atopic</option>
<option value="692.9">692.9-dermatitis contact</option>
<option value="691.0">691.0-diaper rash</option>
<option value="832.00">832.00-dislocation elbow</option>
<option value="995.2">995.2-drug allergy</option>
<option value="380.4">380.4-ear wax</option>
<option value="788.3">788.3-enuresis</option>
<option value="782.1">782.1-non specific exanthem</option>
<option value="780.6">780.6-fever</option>
<option value="487.1">487.1-influenza</option>
<option value="829.0">829.0-fracture</option>
<option value="009.2">009.2-gastroenteritis</option>
<option value="074.3">074.3-hand foot mouth disease</option>
<option value="784.0">784.0-headache</option>
<option value="V20.2">V20.2-health check-up</option>
<option value="785.2">785.2-heart murmur</option>
<option value="228.0">228.0-hemangioma</option>
<option value="708">708-hives</option>
<option value="272.0">272.0-hypercholesterolemia</option>
<option value="401.1">401.1-hypertension</option>
<option value="V05.9">V05.9-immunization vaccination</option>
<option value="684">684-impetigo</option>
<option value="783.3">783.3-feeding difficulty</option>
<option value="774.6">774.6-jaundice</option>
<option value="683">683-lymphadenitis</option>
<option value="457.2">457.2-lymphangitis</option>
<option value="579.8">579.8-intestinal malabsorption</option>
<option value="075.0">075.0-infectious mononucleosis</option>
<option value="M872.00">M872.00-nevus</option>
<option value="388.70">388.70-otalgia earache</option>
<option value="380">380-otitis externa</option>
<option value="382.9">382.9-otitis media</option>
<option value="462">462-pharyngitis</option>
<option value="486">486-pneumonia</option>
<option value="692.6">692.6-poison oak</option>
<option value="477.9">477.9-rhinitis allergic</option>
<option value="057.8">057.8-roseola infantum</option>
<option value="461">461-sinusitis</option>
<option value="848.9">848.9-sprain</option>
<option value="528.0">528.0-stomatitis</option>
<option value="034.0">034.0-strep throat</option>
<option value="V58.3">V58.3-suture and removal</option>
<option value="079.99">079.99-viral syndrome</option>
<option value="520.7">520.7-teething</option>
<option value="771.7">771.7-thrush</option>
<option value="463">463-tonsillitis</option>
<option value="686.1">686.1-umbilical granuloma</option>
<option value="465">465-upper respiratory infection</option>
<option value="599.0">599.0-urinary track infection</option>
<option value="616.10">616.10-vaginitis</option>
<option value="052.9">052.9-varicella</option>
<option value="078.1">078.1-warts</option>
<option value="308.3">308.3-post traumatic stress</option>
<option value="910.7">910.7-splinter</option>
</select>
  </p>
  </card>
</wml>
```

Upon selecting a category, the user finds other sub-categories or appropriate codes in the selected category. The code(s) is or are selected in accordance with the situation or health care event to be reported.

Once one or more codes are entered, they are transmitted from the portable terminal 14 via the wireless network 16 using the Wireless Application Protocol to the gateway 18. The functionality of the gateway 18 includes protocol adapters that change the URL specified in the WAP protocol into a traditional HTTP request over the World Wide Web. The latter can trigger the execution of a script on the server side to access a database or other of information. The implementation is independent of the languages used that may include CGI, Java, Jini, Perl and others. Returning information, the server 22 includes the new WML "deck" to the gateway 18 that in turn generates a WAP response via the wireless network 16 to the portable terminal 14. For example, the application may request a re-entry of the code for verification, or may provide an explanation to the user. Other information that may be transmitted in concurrence with the codes includes other codes (from the same or other codification), age, sex, date of birth, name, or other information.

Example Using cHTML for a PalmVII Wireless PDA

Figure 4A:
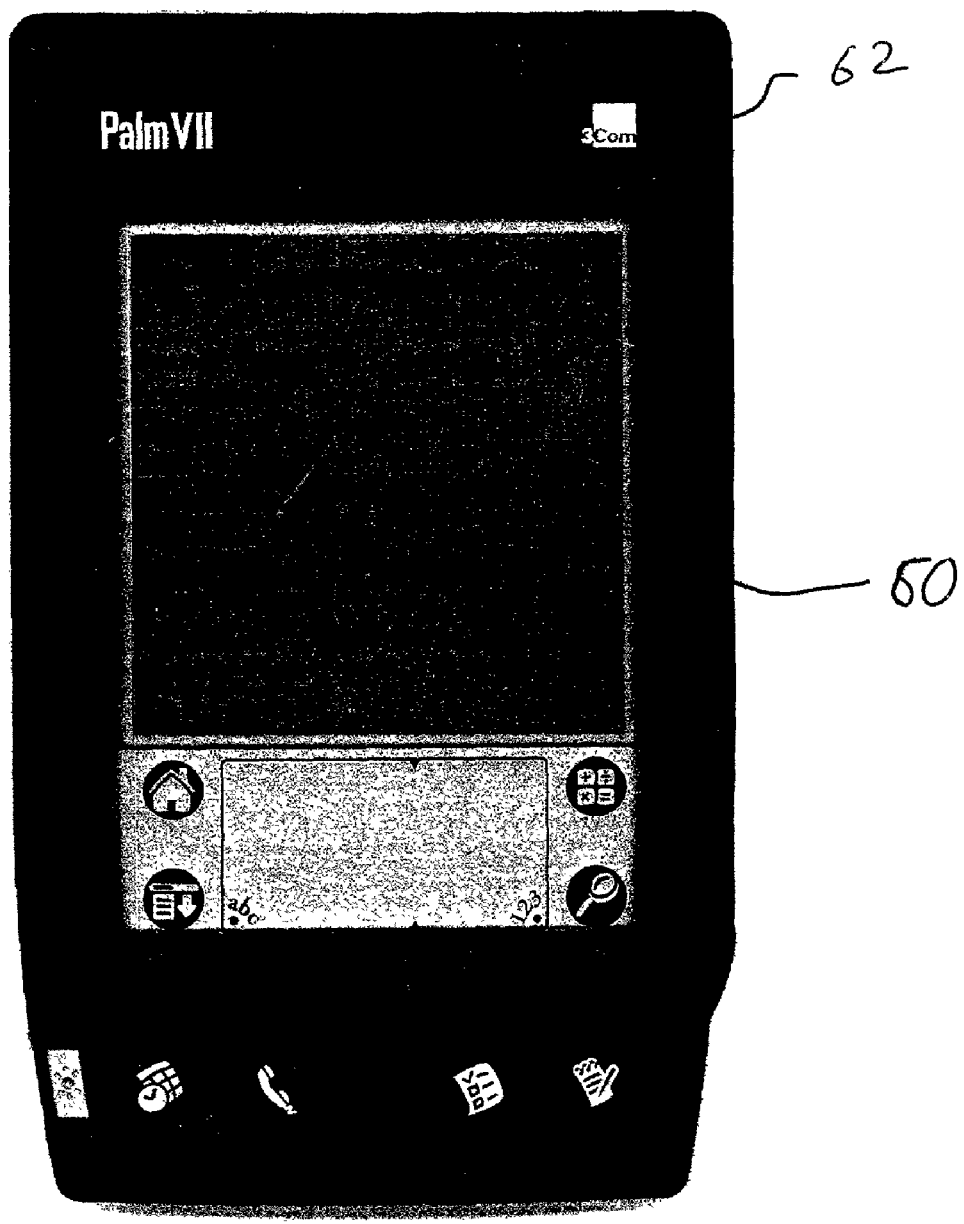
FIGS. 4A-4D illustrate respective healthcare event capture screens for a Palm VII device, according to an exemplary embodiment of the present invention.

FIGS. 4A-4D provide an example which uses other client interfaces for capturing the data. Specifically, FIGS. 4A-4D illustrate exemplary interfaces that may be presented on a personal digital assistant (PDA), such as the Palm VII, utilizing cHTML to capture the relevant data. FIG. 4A illustrates an exemplary data entry interface 60 that may be presented on a PDA 62 to facilitate the entry of event type information and parameters that are then communicated in a wireless manner from the PDA 62 to the application server 22.

Figure 4B:
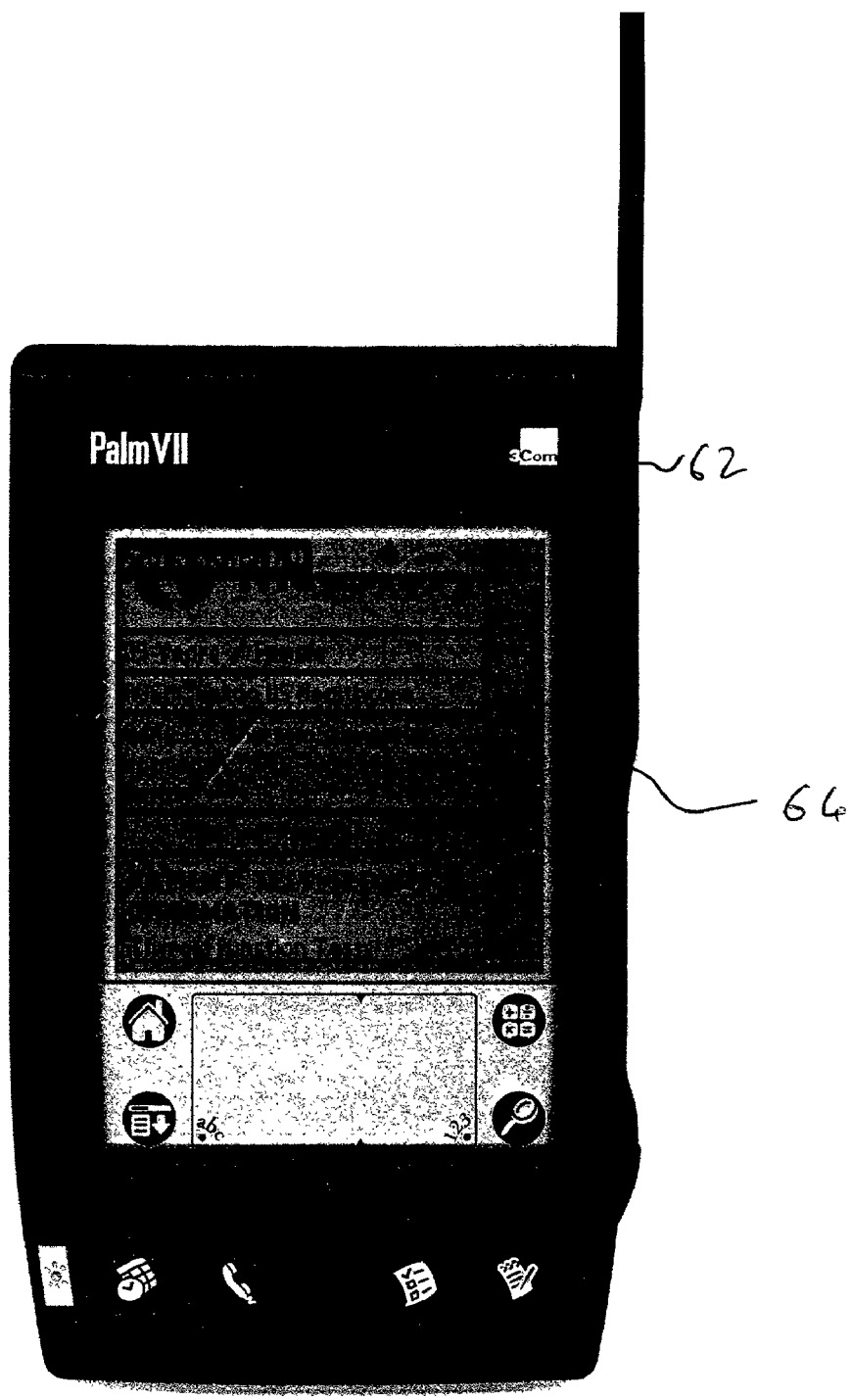
Figure 4C:
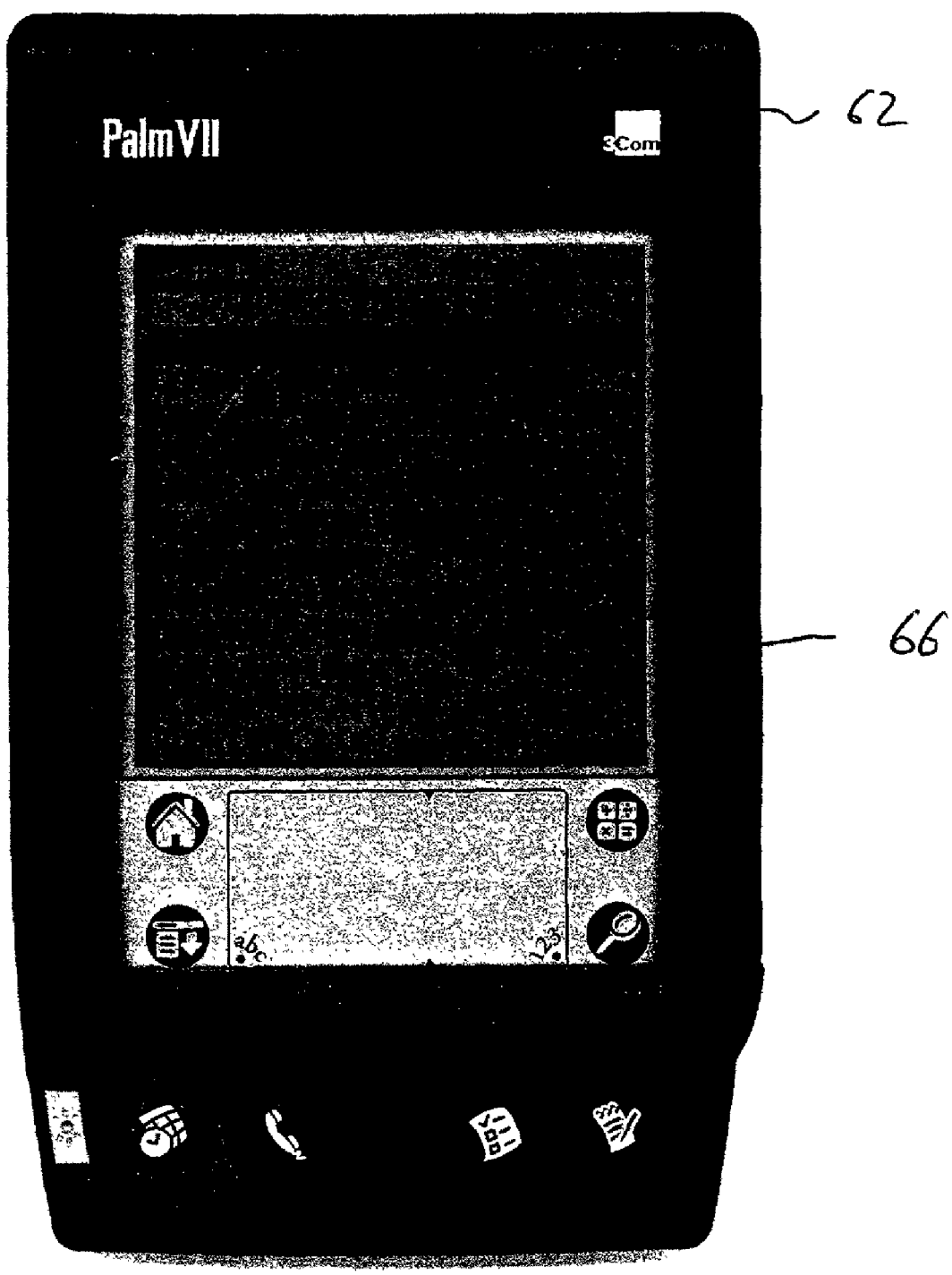
Figure 4D:
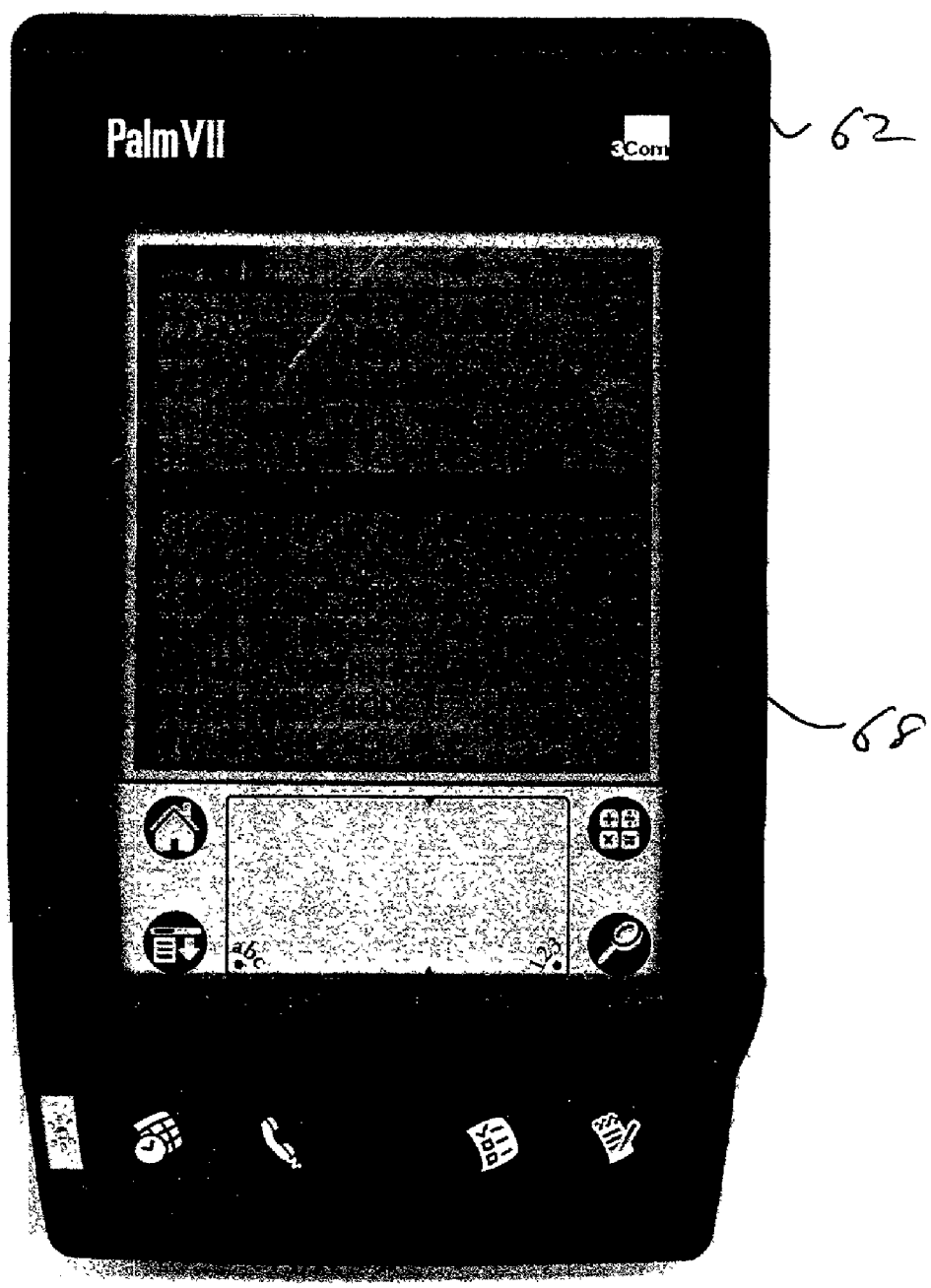

FIG. 4B illustrates an exemplary information interface 64, which displays returned information via which the entered information may be confirmed. FIGS. 4C and 4D illustrate exemplary pull-down menus 66 and 68, that may be invoked for example from the input interface 60 to facilitate the input of meaningful codes. An example of the cHTML that may be utilized to present such codes is provided below.

The codes transmitted may be "Order Codes", i.e. commercial codes used by a specific clinical laboratory company; these are generally mapped to CPT-2000 or CPT-2001 (new edition) codes.

```
<HTML><HEAD>
<meta name="palmcomputingplatform" content="true">
<TITLE>Event Capture</TITLE>
</HEAD><BODY>
<FORM method="get" action="http://medstory.com/palm/visitor.jsp">
<table border="0" cellpadding="0" cellspacing="0">
<tr valign='center'>
<td valign='center'><IMG src="medlogopalm.jpg"></td>
</tr></table>
<BR>
<TABLE align=left border=0 cellPadding=0 cellSpacing=0>
<TR>
<TD><strong>Event Type:</strong></TD>
<TD>
<SELECT id="event" name="event">
<OPTION value="PE">Physician Encounter</OPTION>
<OPTION value="LR" SELECTED>Laboratory Requisition</OPTION>
<OPTION value="RX">Prescription</OPTION>
</SELECT></TD>
<TR>
<TD><STRONG>Condition:</STRONG></TD>
<TD><INPUT id=icdcodes name=icdcodes ></TD>
</TR>
<TR>
<td><strong>Test Req #:</FONT></strong></FONT></td>
<td>
<SELECT id="ordercodes" name="ordercodes">
<option value=" " selected></option>
<option value="7788-7">7788-7-ABO GROUP& RH TYPE</option>
<option value="223-8">223-8-ALBUMIN</option>
<option value="234-9">234-9-ALKALINE PHOSPHATASE (AP)</option>
<option value="823-10">823-10-ALT (SGPT)</option>
<option value="243-11">243-11-AMYLASE</option>
<option value="249-12">249-12-ANTINUCLEAR AB (ANA)</option>
<option value="822-13">822-13-AST (SGOT)</option>
<option value="34388-1">34388-1-BASIC METABOLIC PANEL</option>
<option value="285-14">285-14-BILIRUBIN, DIRECT</option>
<option value="287-15">287-15-BILIRUBIN, TOTAL</option>
</SELECT>
</TD></TR><TR>
<TD><strong>Drug Code:</FONT></strong></FONT></TD>
<TD>
<SELECT id="drugcodes" name="drugcodes">
<option value=" " selected></option>
<option value="514">514-ACE INHIBITORS</option>
<option value="1270">1270-ACNE PRODUCTS</option>
<option value="1032">1032-ADRENAL CORTICOSTEROIDS</option>
<option value="1182">1182-ALLERGENIC EXTRACTS</option>
<option value="513">513-ALPHA AGONISTS/ALPHA BLOCKERS</option>
<option value="633">633-ALZHEIMER-TYPE DEMENTIA</option>
```

```
<option value="352">352-AMINOGLYCOSIDES</option>
<option value="1720">1720-ANALGESICS, GENERAL</option>
<option value="1721">1721-ANALGESICS-NARCOTIC</option>
<option value="1722">1722-ANALGESICS-NON-NARCOTIC</option>
</SELECT>
</td>
</tr>
<TR>
<TD><STRONG>Sex</STRONG></TD>
<TD>
<SELECT name="patientsex">
<option value="Male">Male</option>
<option value="Female" selected>Female</option>
</SELECT>
</TD>
</TR>
<TR>
<TD><STRONG>Age (Y)</STRONG></FONT></TD>
<TD><INPUT id=patientageyears name=patientageyears size="3"></TD>
<TR>
<TD><STRONG>Age (Mo)</STRONG></TD>
<TD><INPUT id=patientagemonths name=patientagemonths size="2"></TD>
</TR>
<TR>
<TD><STRONG>Age (Days)</STRONG></TD>
<TD><INPUT id=patientagedays name=patientagedays size="2"></TD>
</TR>
<TR>
<td><STRONG>Target:</STRONG></td>
<TD>
<SELECT id="target" name="target">
<option value="Patient" selected>Patient</option>
<option value="Physician">Physician</option>
</SELECT>
</TD></TR>
<TR>
<TD><STRONG>Health Plan:</STRONG></TD>
<TD>
<SELECT id="healthplan" name="healthplan">
<option value=1 selected>AUSHC Aetna US Healthcare</option>
<option value=2>CGM CIGNA All Plans</option>
<option value=7>Foundation Health Systems</option>
<option value=5>Kaiser Permanente</option>
</SELECT>
</TD></TR>
<TR>
<TD valign='center'><input id="Run" name="Run" value="ZeroSearch" type="submit"></TD>
</TR></TABLE></FORM></BODY></HTML>
```

In this example, the user will interact with the Palm VII cHTML display controls to enter the event type and parameters. When a "ZeroSearch" button such as that depicted in the FIG. 4A is clicked, the cHTML form is posted to the application server 22 through a proxy server that connects the wireless network 16 to the Internet. The cHTML form and its values are submitted and processed by the application server 22 just as a standard HTML form would be processed. The response from the server is formatted in cHTML and contains verification of the submitted values.

From an application example perspective, the healthcare data in the code received by the application server 22, in combination with other information if available, will help determine a set of preferred patient education information and compose a personal "MyMedstory" (trade mark) document for the patient in question, as described in the above referenced U.S. patent application. The delivery of this "document" may take multiple forms, including but not limited to delivery on WAP platforms that include mobile telephones and other appliances. The healthcare provider entering the code may also have access to the same document or a modified one, according to the chosen application logic.

The described "WirelessMed" system can be used to transmit information to any and all end users that may need the information, in addition to the patient. This includes, but is not limited to, insurance and managed care companies, medical record companies, other medical service organizations, other physicians or content distribution services, as described in the above referenced U.S. patent application.

Security is an essential component of any medical information system. In the context of the present invention, security of information may be achieved in a variety of ways including, but not limited to, encryption and digital signatures and authentication. Such capabilities can be expected to be bundled with the cellular technology provider software.

The method and system of the invention provide a number of features. Firstly, the system provides a new user experience for physicians or healthcare providers. The system provides a communication mechanism for transmitting useful healthcare information to the various players in the delivery chain. This mechanism allows for either concurrent or retrospective coding. The system facilitates relaying of the information to an Internet-based infrastructure without a traditional computer. The system provides two-way interactivity with the client being "called" as well, which allows for verification of information and other interactions that may be deemed useful. The information transmitted might, for example, require verification (re-entry) or additional information in order for the server to proceed with its task. Two-way communication devices such as cellular phones or personal communication assistants allow for such interactions. For example, if the system is used to enter an order for a clinical laboratory test, the initial data may have to be supplemented in order for the order to go through; as another example, certain types of information may require more data from the user than was inputted, such data including, but are not limited to, other and additional codes to describe the clinical condition.

This feature can be implemented, for example, in the application server 22. The system further provides for integration of voice and data, increased ease-of-use and deployment with standardization of the interface, and mobility and ubiquity. Standard interfaces may be developed for large or smaller groups of users. For example, a "superbill" (defined for example as the most common set) of codes for a given specialty or subspecialty may be pre-defined and all physicians or providers in a given network or group may then use the same superbill. Such superbills may vary according to regions or populations, for example. Since the devices are hand-held or portable, and can carry many other functions, they are highly mobile, allowing for the users to always have rapid access to critical information, such as lists of codes. Since the wireless network can support as wide an area as necessary, codes can be entered from any location supported by the networks, making the solution ubiquitous (for example, a provider may be changing hospital, region or even country).

For example, for verification purposes, the communication may be done by voice, whereby the system reads back the entry and asks for confirmation either digitally or by voice as well; as another example, after entry of one or several codes, the system may require further data. This request can be placed by voice.

FIG. 5 is a flow chart illustrating a method 40, according to exemplary embodiment of the present invention, of communicating healthcare information to and from a portable handheld device. FIG. 5 illustrates exemplary activity on both a server side and a client side, the activities illustrated in this flow chart having been described above.

Thus a method and system for communicating health care information to and from a portable, hand held device have been described. Although the invention has been described with reference to specific exemplary embodiments, it will be evident that various modifications and changes may be made to these embodiments without departing from the broader spirit and scope of the invention. Accordingly, the present specification and drawings are to be regarded in an illustrative rather than a restrictive sense.

What is claimed is:

1. A method of communicating healthcare information, the method comprising:
    displaying a set of codes corresponding to respective healthcare data, the respective healthcare data including a plurality of medical diagnoses which correspond to at least one code;
    storing the set of codes and the plurality of medical diagnoses in a memory of a portable terminal;
    detecting selection of a subset of a displayed set of codes that corresponds to a medical diagnosis relevant to a patient; and
    wirelessly transmitting a selected subset of the displayed set of codes from the portable terminal to a server system via a first network capable of providing communication between the portable terminal and the server system, wherein said wirelessly transmitting causes healthcare data corresponding to the selected subset of the displayed set of codes to be provided via a second network capable of providing communication between the server system and a patient accessible device.

2. The method of claim 1, wherein the portable terminal is a cellular telephone having an on-board memory, the set of codes including one of an International Statistical Classification of Diseases and Related Health Problems, 9th Revision, Clinical Modification (ICD-9CM) diagnosis code, an International Statistical Classification of Diseases and Related Health Problems, 10th Revision, Clinical Modification (ICD-10CM) diagnosis code or a Healthcare Common procedure Coding System/Current Procedural Terminology (HCPCS/CPT) code stored in the on-board memory.

3. The method of claim 1, wherein the at least one code is transmitted via a first, wireless network.

4. The method of claim 3, wherein the first, wireless network is one of a Code Division Multiple Access (CDMA) network, a Global System for Mobile Communicatins (GSM) network, a Time Division Multiple Access (TDMA) network or a Cellular Digital Packet Data (CDPD) network.

5. The method of claim 3, wherein a gateway connects the first, wireless network to the second network.

6. The method of claim 5, wherein the second network comprises the Internet/World Wide Web.

7. The method of claim 5, wherein healthcare data corresponding to a transmitted selected subset of the displayed codes is associated with corresponding healthcare information in a database, and wherein said corresponding healthcare information is transmitted, via the second network, to a patient on which diagnosis was performed.

8. The method of claim 1, wherein the at least one code is transmitted using Wireless Mark-up Language (WML).

9. A machine-readable medium comprising instructions which, when executed by a machine, cause the machine to perform operations comprising:
    displaying a set of codes and medical diagnoses on a portable terminal, one or more of the set of codes corresponding to respective healthcare data, the respective healthcare data including the medical diagnoses one or more of which corresponds to at least one code, wherein the set of codes and the medical diagnoses are stored in a memory of the portable terminal;
    detecting selection of a subset of the set of codes that corresponds to a comprehensive medical diagnoses of patient; and
    wirelessly transmitting a selected subset of the set of codes to a server system via a first network capable of providing communication between the portable terminal and a server system, wherein said wirelessly transmitting the selected subset of the set of codes causes at least some of the medical diagnoses to be provided to the patient via a second network capable of providing communication between the server system and a patient accessible device.

* * * * *

UNITED STATES PATENT AND TRADEMARK OFFICE
CERTIFICATE OF CORRECTION

| | | |
|---|---|---|
| PATENT NO. | : 7,689,438 B1 | Page 1 of 1 |
| APPLICATION NO. | : 09/713962 | |
| DATED | : March 30, 2010 | |
| INVENTOR(S) | : Alain T. Rappaport et al. | |

It is certified that error appears in the above-identified patent and that said Letters Patent is hereby corrected as shown below:

In column 12, line 22, in Claim 4, delete "Communicatins" and insert -- Communications --, therefor.

Signed and Sealed this
Twenty-fourth Day of May, 2011

David J. Kappos
*Director of the United States Patent and Trademark Office*